United States Patent [19]

Itoh

[11] Patent Number: 4,920,275
[45] Date of Patent: Apr. 24, 1990

[54] PARTICLE MEASURING DEVICE WITH ELLIPTICALLY-SHAPED SCANNING BEAM

[75] Inventor: Yuji Itoh, Chigasaki, Japan

[73] Assignee: Canon Kabushiki Kaisha, Tokyo, Japan

[21] Appl. No.: 292,267

[22] Filed: Dec. 30, 1988

[51] Int. Cl.$^5$ .............................................. G01N 15/06
[52] U.S. Cl. ...................................... 250/574; 356/338
[58] Field of Search ............... 250/564, 565, 574, 575; 356/338–343, 441, 442

[56] References Cited

U.S. PATENT DOCUMENTS 3,918,812 11/1975 Holm .
4,577,964 3/1986 Hansen, Jr. .......................... 356/338
4,636,075 1/1987 Knollenberg ........................ 356/338
4,827,144 5/1989 Zaitsu et al. .......................... 250/574

Primary Examiner—David C. Nelms
Assistant Examiner—Khaled Shami
Attorney, Agent, or Firm—Fitzpatrick, Cella, Harper & Scinto

[57] ABSTRACT

A particle measuring device having a light source, scanning means for optically scanning a light from the light source in a direction intersecting the direction of passage of particles to be examined in a portion to be examined through which the particles to be examined pass, means for making the shape of the scanning light applied to the particles to be examined into a shape longer than the length of the particles to be examined in the direction of passage of the particles to be examined, and light receiving means for receiving the light from the portion to be examined.

13 Claims, 2 Drawing Sheets

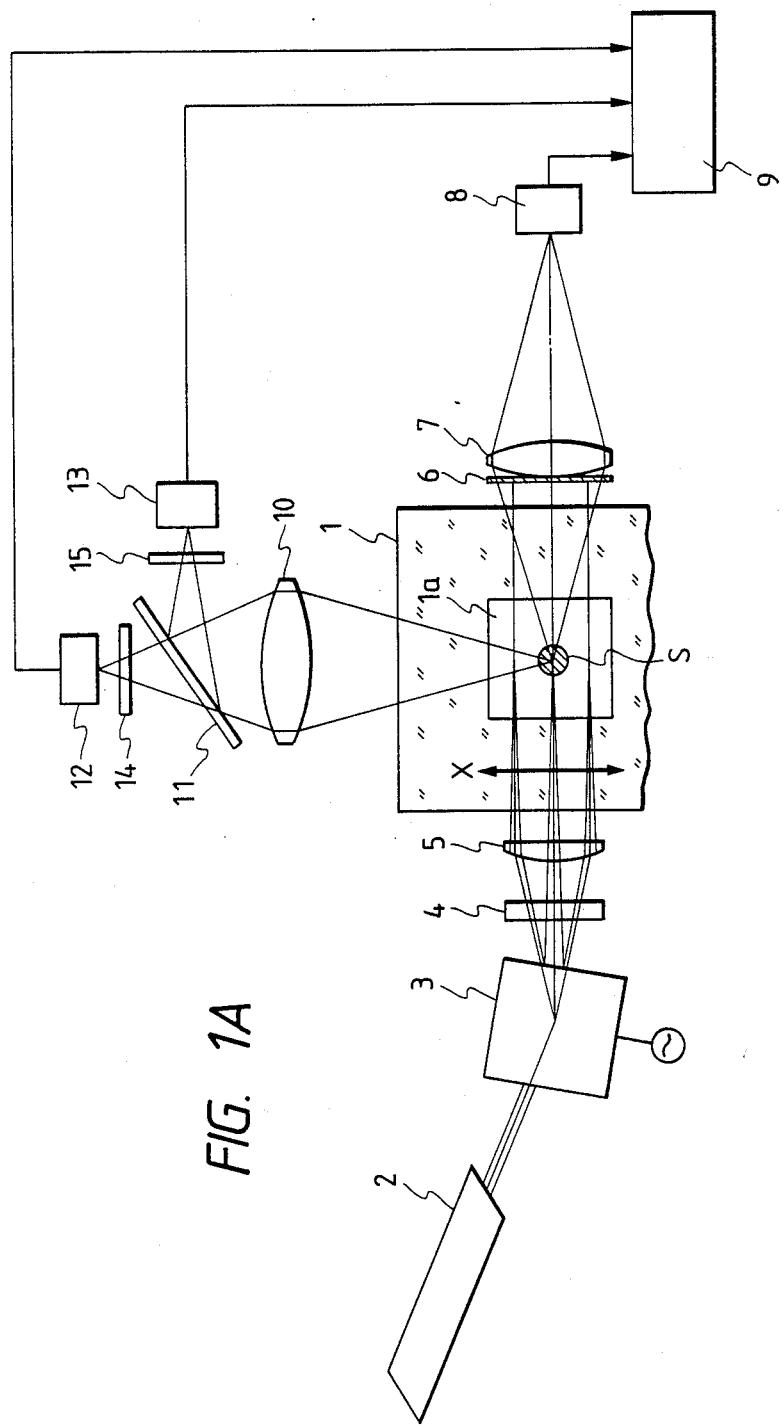
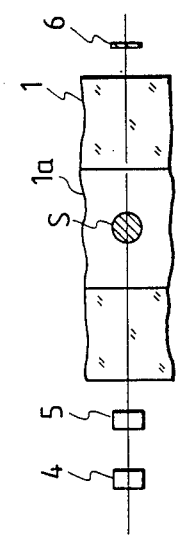
FIG. 1A
FIG. 1B

4,920,275

PARTICLE MEASURING DEVICE WITH ELLIPTICALLY-SHAPED SCANNING BEAM

BACKGROUND OF THE INVENTION

1. Field of the Invention

This invention relates to a particle analyzing device such as a flow cytometer for applying a light to flowing particles to be examined and detecting the optical reaction thereof, thereby accomplishing measurement of the particles to be examined.

2. Related Background Art

The flow cytometer is a device for applying for example, a laser beam to a cell floating solution flowing at a high speed, i.e., sample fluid, detecting the photoelectric signal by the scattered light or fluorescence thereof and making clear the nature and structure of cells, and is used in the fields of cytochemistry, immunology, hematology, oncology, genetics, etc.

In the conventional particle measuring device used in such flow cytometer or the like, sample fluid flows through the flow-through portion of the central portion of a flow cell having, for example, a minute square cross-section of 200 $\mu m \times 200$ $\mu m$ while being wrapped in sheath liquid. An irradiating light such as a laser beam is applied to minute particles to be examined such as blood cells in the sample fluid passing one after another at a high speed, and forward scattered light, sideways scattered light, fluorescence or transmitted light produced as a result is measured, whereby measured values of several kinds of parameters are obtained with respect to several tens of thousand to several hundreds of thousands of particles to be examined. These numerous measured data are represented in the form of a histogram or a cytogram and subjected to statistical processing, whereby, analysis of the particles to be examined is effected and for example, the discrimination between the kinds of particles and the tendency of the natures thereof can be grasped.

Heretofore, design has been made such that particles to be examined pass through a light beam fixed and applied at a position to be examined, but usually a laser beam having a Gaussian strength distribution is used as an irradiating light source and therefore, the fixed light beam does not have a uniform strength distribution. Consequently, the particles to be examined have not always passed through the peak position of the Gaussian strength distribution due to the drift thereof into a direction orthogonal to the flow of the particles to be examined in the sample stream caused by various unstable factors of the device, or the drift thereof into a direction orthogonal to the flow caused by the disturbance of the sample stream itself, but light energy applied to each particle to be examined has differed. This has led to the problem that fluctuation or irregularity of measured values occurs to reduce the accuracy of analysis.

Also, discretely from the above-described flow cytometer, devices which can obtain two-dimensional information of individual particles to be examined are described in U.S. Pat. No. 3,918,812 and Japanese Laid-Open Patent Application No. 62-76462. In these devices, a beam spot smaller than the particles to be examined is continuously optically scanned at a high speed in a direction intersecting the flow of the particles to be examined, and the particles to be examined are substantially two-dimensionally scanned, whereby two-dimensional image information is obtained.

In these devices, however, a great deal of data storage memory is necessary per particle and this is not suitable for a flow cytometer for statistically effecting analysis, in respect of cost and processing speed.

SUMMARY OF THE INVENTION

It is an object of the present invention to provide a particle measuring device which can irradiate particles to be examined with a uniform intensity without being affected by the deviation of the passage position of the particles to be examined, and can obtain stable measured values.

It is another object of the present invention to provide a particle measuring device for irradiating particles to be examined with a scanning light in which the particles to be examined can flow at a high speed and which is high in measuring speed.

It is still another object of the present invention to provide a particle measuring device for irradiating particles to be examined with a scanning light in which it is not necessary to enhance the light scanning speed and which is inexpensive.

It is yet still another object of the present invention to provide a particle measuring device in which a particle is optically scanned a plurality of times and a plurality of data are obtained per particle and which is high in reliability and can obtain measured values of high sensitivity.

DESCRIPTION OF THE DRAWINGS

FIG. 1A is a view of an embodiment of the particle measuring device of the present invention as seen in a planar direction.

FIG. 1B is an optical path view in a flow cell as seen in a sideways direction orthogonal to FIG. 1A.

DESCRIPTION OF THE PREFERRED EMBODIMENTS

Figure 2:
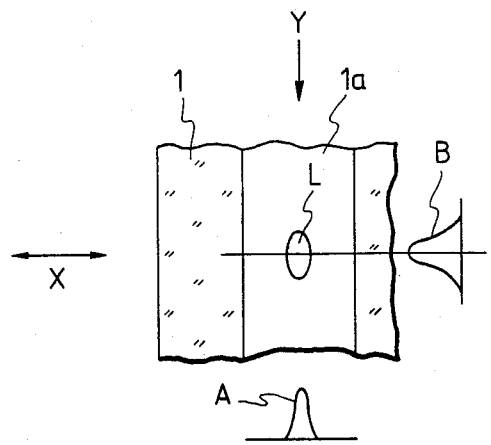
FIG. 2 shows the relation between the shape and the strength distribution of a scanning light.

Some embodiments of the present invention will hereinafter be described in detail with reference to the drawings.

Sample fluid is caused to flow as a fine stream to the central portion of the flow-through portion 1a of a flow cell 1 by the laminar sheath flow principle, and particles S to be examined such as biological cells or latex particles in the sample fluid pass therethrough one by one. A laser source 2 is disposed in a direction orthogonal to the flow-through portion 1a and a laser light emitted from this laser source 2 may be condensed on the flow cell 1 through an A/O light modulator 3 and cylindrical lenses 4 and 5. The cylindrical lens 4 has refractive power only in the direction of flow of the sample fluid, and the cylindrical lens 5 has a refractive power only in a direction orthogonal to the flow of the sample fluid, and is adapted to have a focus at the center of the A/O light modulator 3 in the plane of the drawing sheet of FIG. 1A. The cylindrical lenses 4 and 5 are in a form interchangeable with cylindrical lenses of different F-number, and can vary the shape of the scanning light in the portion to be examined in vertical and horizontal directions in conformity with the size of the particles S to be examined and the purpose of measurement.

A stopper 6, a condensing lens 7 and a photodetector 8 are arranged in the optical path at that side opposite to the flow cell 1. The stopper 6 performs the function of preventing the direct light of the scanning light or the light transmitted through the particle to be examined from entering the photodetector 8, and only the forward scattered light from the particle S to be examined may be detected by the photodetector 8. A detecting optical system is provided in a direction orthogonal to the optical path from the flow cell 1 to receive fluorescence and sideways scattered light emitted simultaneously with the forward scattered light. The fluorescence and sideways scattered light condensed by a condensing lens 10 are transmitted through and reflected by a dichroic mirror 11, respectively, and the fluorescence and the scattered light are separated from each other. The fluorescence transmitted through the dichroic mirror 11 has its intensity detected by a barrier filter 14 and a photodetector 12, and the sideways scattered light reflected by the dichroic mirror 11 has its intensity detected by a barrier filter 15 and a photodetector 13. The outputs of these photodetectors 12 and 13 are connected to a memory calculation circuit 9 with the output of the aforementioned photodetector 8 for detecting the forward scattered light.

The A/O light modulator 3 can change the degree of deflection of the incident light by a control frequency and therefore, by continuously varying the control frequency at a predetermined period, the laser light emitted from the laser source 2 is light-scanned by the A/O light modulator 3. The scanning light scanned here is condensed into the flow-through portion 1a of the flow cell 1 by the cylindrical lenses 4 and 5. By placing the vicinity of the center of the A/O light modulator 3 at the forward focus position of the cylindrical lens 5, it is possible to scan the laser light in X direction in a telecentric state and apply it to the particle S to be examined and therefore, it becomes possible to apply the laser light always at a maximum amount of irradiation even if the particle S to be examined drifts in a direction orthogonal to the flow. The light scanning means is not limited to the A/O light modulator, but may also be scanning means such as a rotational mirror or a galvano mirror.

By the selection of the cylindircal lenses 4 and 5 used, the shape of the scanning light applied to the particle S to be examined can be made into any shape in which the length thereof in the direction of passage of the particle to be examined is longer than the particle to be examined, and in FIG. 2, a case where the shape of the scanning light is made into an elliptical shape having a major axis in the direction of flow i.e., Y direction, is shown as an example. The elliptical scanning light L is continuously scanned at a high speed in X direction. In FIG. 2, A and B show the intensity distribution of the respective imaging beams L in the central cross-sections thereof.

The relation between the particle S to be examined and the light scanning will now be described with reference to FIG. 3. FIGS. 3A and 3B show the relation between the particle S to be examined flowing through the flow-through portion 1a and the shape of the scanning beam, and there are shown the relation between the particle to be examined and the scanning beam at the lapse of light scanning times t1, t2 and t3.

Figure 3A:
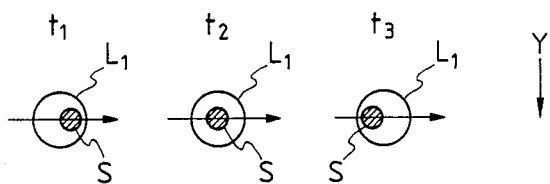
FIGS. 3A and 3B illustrate the relation between the shape of the scanning light and particle to be examined.

FIG. 3A shows an embodiment of the present invention in which the shape of the scanning light L1 is a circle having a diameter greater than that of the particle S to be examined. The scanning light L1 can uniformly irradiate the particle S to be examined with maximum light energy even if the particle S to be examined is caused to flow minutely in Y direction when the particle to be examined is irradiated with light scanning being uniformly repeated in the direction of arrow in the flow-through portion. Also, even if the flow position of the particle S to be examined drifts in X direction, the particle S to be examined is irradiated with uniform intensity. Consequently, the measured value obtained is free of irregularity and high in reliability.

Assuming in FIG. 3A that the shape of the scanning light L1 is a circle of a relatively small diameter so that the light energy density may not weaken, a case where the light scanning speed is great relative to the speed in the flow direction Y, that is, a case where the scanning speed is very great or the flow of the particle S to be examined is very slow, is fit. In such case, the movement of the particle to be examined in Y direction is small during one cycle of scanning and therefore, the particle to be examined can be uniformly irradiated with a maximum light intensity with respect to Y direction. If the shape of the scanning light L1 is made into a circle having too large a diameter, the light energy density of the scanning light will become small and the light energy applied to the particle S to be examined will become small, and the measurement sensitivity will be reduced.

Thus, by causing an irradiating light of a predetermined shape to scan in a direction intersecting the direction of flow of the particle to be examined, the particle to be examined can be uniformly irradiated with a maximum intensity even if the passage position of the particle to be examined deviates and therefore, a measured value of high stability can be obtained.

Figure 3B:
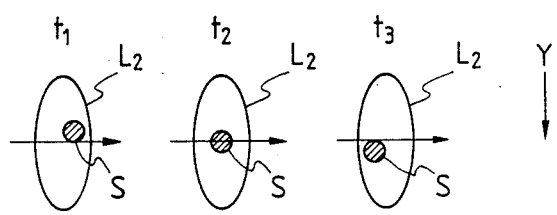

FIG. 3B shows another embodiment or more preferred form of the present invention in which the shape of the scanning light L2 is made into an elliptical shape having a major axis in the direction of flow. By adopting such an elliptical shape, as compared with the circle shown in FIG. 3A, the light energy density can be made great and the size in the direction of flow can be made large. The form shown in FIG. 3B is particularly useful when the flow speed of the particle S to be examined is high or when the light scanning speed is low. The position in which the particle S to be examined impinge on the light beam in the flow direction Y differs during one cycle of scanning, i.e., t1, t2 and t3. However, the shape of the scanning light L2 is longer in the flow direction Y of the particle to be examined and further, the light energy distribution in the flow direction is substantially uniform and therefore, the variation in the light intensity in the flow direction Y is almost null and during one cycle of scanning, uniform light energy of substantially maximum intensity relative to the direction of flow can be applied to the particle S to be examined. Further, it also becomes possible to obtain the data by a plurality of times of light scanning for the same particle and thus, more accurate measurement can be expected. Which of these plural measured values should be adopted as the analysis data is variously conceivable depending on the case. For example, if the mean value of a plurality of measured values is adopted, there will be obtained analysis data of high reliability. In such case, it will be more preferable to omit the measured values obtained first and last. Or, if the greatest one of the plurality of measured values is adopted, it will be possible to obtain analysis data of high measurement sensitivity. This is because as the light application intensity is higher, the measured value obtained becomes greater, that is, there is obtained a measured value of high sensitivity when the particle to be examined is irradiated with the portion of maximum strength in the central portion of the Gaussian strength distribution of the scanning light.

By thus making the shape of the scanning light into an elliptical shape, as compared with FIG. 3A, there is provided a device which can enhance the measuring speed and can deal with a great quantity within a short time. Or there is provided an inexpensive device in which it is unnecessary to enhance the light scanning speed. The shape of the scanning light is not limited to regular ellipse, but may be a vertically longer shape such as a substantially elliptical shape or a rectangular shape.

Figure 4:
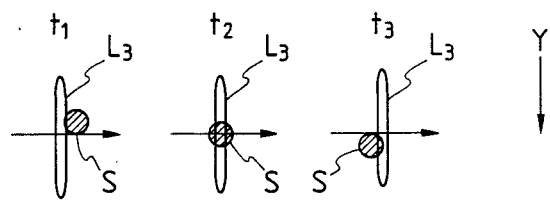
FIG. 4 illustrates another embodiment of the present invention.

FIG. 4 illustrates a third embodiment of the present invention in which slit-scan is possible. The length in the flat direction of a slit-shaped scanning light L3 made by the selection of the cylindrical lenses 4 and 5 is set to a value smaller than the diameter of the particle S to be examined. Also, the length of the scanning light L3 in the direction of flow is set to to a value greater than the diameter of the particle to be examined. Thus, as previously described, measurement is not affected by the deviation of the flow position of the particle to be examined and therefore, measurement of higher accuracy than by the slit-scan system of the conventional particle measuring device becomes possible. In this case, detection of the structure in the scanning direction also becomes possible for the particle S to be examined.

The method of carrying out the analyzing process by the use of a histogram, a cytogram or the like on the basis of the analysis data obtained in the above-described manner is similar to the prior art, and calculation is done by the memory calculation circuit 9.

The present invention is applicable not only to detection of scattered light and fluorescence, but also to detection of transmitted light.

I claim:

1. A particle measuring device provided with:
a light source;
scanning means for optically scanning a light from said light source in a direction intersecting the direction of passage of particles to be examined in a portion to be examined through which the particles to be examined pass;
means for making a shape of the scanning light applied to the particles to be examined into a shape longer than the length of the particles to be examined in the direction of passage of the particles to be examined; and
light receiving means for receiving the light from the portion to be examined.

2. A particle measuring device according to claim 1, wherein the shape of said scanning light is an elliptical shape having a major axis in the direction of passage of the particles to be examined.

3. A particle measuring device according to claim 2, wherein the shape of said scanning light is shorter in the length in the scanning direction than the particle diameter of the particles to be examined.

4. A particle measuring device according to claim 2, wherein said scanning light is made into an elliptical shape by a cylindrical lens.

5. A particle measuring device according to claim 4, having a first cylindrical lens having a generatrix direction in the direction of passage of the particles to be examined, and a second cylindrical lens having a generatrix direction in a direction orthogonal to the direction of passage.

6. A particle measuring device according to claim 1, wherein said scanning means is an optical system including an A/O light modulator.

7. A particle measuring device according to claim 6, wherein the central position of said A/O light modulator is substantially at the focus position of said first cylindrical lens.

8. A particle measuring device according to claim 6, wherein said optical system is a telecentric optical system.

9. A particle measuring device according to claim 1, wherein said particles to be examined pass one by one.

10. A particle measuring device according to claim 9, wherein said portion to be examined is a flowthrough portion in a flow cell.

11. A particle measuring device according to claim 1, wherein a stopper for cutting the scanning light is provided in the optical path rearwardly of said portion to be examined.

12. A particle measuring device according to claim 11, wherein the shape of said stopper is elongate in the scanning direction.

13. A particle measuring device according to claim 1, wherein the light from said portion to be examined is scattered light and/or fluorescence produced by the application of light to the particles to be examined.

* * * * *